US010124057B2

(12) United States Patent
Chen et al.

(10) Patent No.: US 10,124,057 B2
(45) Date of Patent: Nov. 13, 2018

(54) METHOD OF QUICKLY PRODUCING ANTIBODIES AGAINST AVIAN INFLUENZA AND MAINTAIN ANTIBODY TITER OF DUCK

(71) Applicants: Zhaoqing Dahuanong Biological Medicine Co., Ltd, Zhaoqing (CN); South China Agricultural University, Guangzhou (CN)

(72) Inventors: Ruiai Chen, Zhaoqing (CN); Aiguo Zhang, Zhaoqing (CN); Yufu Liu, Zhaoqing (CN); Jiahua Xu, Zhaoqing (CN); Shuqiong Zhang, Zhaoqing (CN); Wenke Huang, Zhaoqing (CN); Daxing Wu, Zhaoqing (CN); Shichang Liao, Zhaoqing (CN)

( * ) Notice: Subject to any disclaimer, the term of this patent is extended or adjusted under 35 U.S.C. 154(b) by 0 days.

(21) Appl. No.: 15/444,305

(22) Filed: Feb. 27, 2017

(65) Prior Publication Data

US 2017/0246289 A1 Aug. 31, 2017

(30) Foreign Application Priority Data

Feb. 25, 2016 (CN) .......................... 2016 1 0105195

(51) Int. Cl.

*A61K 39/145* (2006.01)
*C12N 7/00* (2006.01)
*A61K 39/12* (2006.01)
*A61K 39/00* (2006.01)

(52) U.S. Cl.

CPC ............ *A61K 39/145* (2013.01); *A61K 39/12* (2013.01); *A61K 2039/5252* (2013.01); *A61K 2039/54* (2013.01); *A61K 2039/543* (2013.01); *A61K 2039/545* (2013.01); *A61K 2039/552* (2013.01); *A61K 2039/55566* (2013.01); *A61K 2039/575* (2013.01); *C12N 2760/16134* (2013.01); *C12N 2760/16171* (2013.01)

(58) Field of Classification Search

None

See application file for complete search history.

(56) References Cited

U.S. PATENT DOCUMENTS

| | | | | |
|---|---|---|---|---|
| 5,676,950 A * | 10/1997 | Small, Jr. | ............. | A61K 39/145<br>424/199.1 |
| 2008/0032921 A1* | 2/2008 | Alexander | ........... | A61K 39/145<br>424/526 |
| 2010/0255029 A1* | 10/2010 | Bublot et al. | ........ | A61K 39/145<br>424/199.1 |
| 2017/0246289 A1* | 8/2017 | Chen | .................... | A61K 39/145 |

OTHER PUBLICATIONS

Bahgat et al. (Journal of Virological Methods. 2009; 159: 244-250).*

Xiaowen et al. (Vaccine. 2009; 27: 5628-5632).*

* cited by examiner

*Primary Examiner* — Shanon A. Foley

(74) *Attorney, Agent, or Firm* — Wayne & King LLC

(57) ABSTRACT

The present invention provides a method for enabling ducklings to quickly produce anti-avian influenza antibodies and maintain antibody titer, including: step 1) the first immunization is performed on ducklings at the age of 5 to 15 days: each duckling is inoculated with an avian influenza inactivated antigen in an abdomen, and simultaneously intramuscularly or subcutaneously immunized with an avian influenza inactivated oil-emulsion vaccine. In the method, through the double effects of intraperitoneal inoculation with the inactivated antigen and intramuscular or subcutaneous injection with the inactivated oil-emulsion vaccine on the ducklings, the ducklings can quickly produce an immune response so as to quickly produce the anti-avian influenza antibodies; and the immune dead time of the ducklings immunized with the avian influenza inactivated vaccine can be effectively reduced by more than 7 days.

10 Claims, No Drawings

METHOD OF QUICKLY PRODUCING ANTIBODIES AGAINST AVIAN INFLUENZA AND MAINTAIN ANTIBODY TITER OF DUCK

CROSS-REFERENCE TO RELATED APPLICATIONS

This application claims priority to, Chinese Patent Application No. 201610105195.5 with a filing date of Feb. 25, 2016. The content of the aforementioned application, including any intervening amendments thereto, is incorporated herein by reference.

TECHNICAL FIELD

The present invention relates to the technical field of waterfowl breeding, and in particular relates to a method for enabling ducklings to quickly produce anti-avian influenza antibodies and maintain antibody titer.

BACKGROUND

Since the end of the last century, the virulence of a high-pathogenicity H5 subtype epidemic strain to the waterfowl has been gradually increased, and also has led to the disease and death of the waterfowl like the terrestrial poultry. The waterfowl itself is not only a library of influenza viruses, but also a susceptible host of influenza viruses.

An acquired immune system of the fowl consists of bursal derived immunity and thymus derived immunity. Antibodies are produced through the stimulation of antigens, and three types of antibodies are produced through the cellular immune response: IgM, IgY and IgA. Li Ning team finds that the number of immune-related genes of ducklings is equal to that of immune-related genes of chickens, both obviously less than the number of immune-related genes of mammals, but the number of β-defensin genes and butyrophilin-like repertoires genes of the ducklings is obviously greater than that of the chickens. Since the poultry differs from the waterfowl in characteristics of immune response, the increasing speed and the titer of antibodies of ducklings immunized with avian influent inactivated vaccines are obviously lower than those of the chicken immunized with same. For example, after the chickens are immunized with the avian influenza inactivated vaccine, the antibody titer can reach 3 to 5 Log2, 5 to 8 Log2 and 8 to 10 log2 respectively on $7^{th}$ day, $14^{th}$ days and $21^{st}$ days, and the antibody titer is highest on $28^{th}$ to $35^{th}$ days; however, after the ducklings are immunized with the avian influenza inactivated vaccine, the antibody titer can reach 2 to 3 Log2, 3 to 6 Log2 and 5 to 8 Log2 respectively on $7^{th}$ day, $14^{th}$ day and $21^{st}$ day, and the highest antibody titer of 6 to 9 Log2 can be achieved on 28th to 35th days and can be maintained for 2 to 3 months.

Although there is a difference in the reports about the law of growth and decline for maternal antibodies of the ducklings, generally the titer of the avian influenza maternal antibodies of the ducklings is decreased from 8 to 10 Log2 for the ducklings at the age of one day to a titer less than a critical point (4 to 6 Log2) for the ducklings at the age of 7 to 9 days, and to 0 to 2 Log2 for the ducklings at the age of 15 to 28 days. The maternal antibodies may interfere with the immune effect of the avian influenza inactivated vaccine on the ducklings and even may produce immuno-suppression seriously. Since the breeding ducklings generally have relatively high avian influenza antibodies, the produced ducklings essentially have relatively high maternal antibodies which generally may protect the ducklings at the age of 1 to 15 days and may help the ducklings to resist the infection of the high-pathogenicity avian influenza viruses. When the ducklings at the age of more days receive the avian influenza immunization, the immune dead time is excessively long, which may increase the risk of the ducklings infected with the high-pathogenicity avian influenza viruses. Therefore, the ducklings may be generally immunized with the avian influenza inactivated vaccine at the age about 10 days. Since the antibodies are slowly produced after the ducklings are immunized with the avian influenza inactivated vaccine, the ducklings immunized with the avian influenza vaccine have an immune dead time about two weeks. During this period of time, the avian influenza valence is low, and the ducklings are susceptible to the avian influenza infection, resulting in serious economic loss. How to technically enable the ducklings immunized with the avian influenza vaccine to quickly produce antibodies and maintain the antibody level has an important significance on the duck farming industry.

SUMMARY

In order to overcome the defects in the prior art, an objective of the present invention is to provide a method for enabling ducklings to quickly produce anti-avian influenza antibodies and maintain antibody titer.

In order to achieve the above-mentioned objective, the present invention adopts a technical solution as follows:

a method for enabling ducklings to quickly produce anti-avian influenza antibodies and maintain antibody titer includes: step 1) immunizing ducklings at the age of 5 to 15 days by inoculating each duckling with an avian influenza inactivated antigen into an abdominal cavity, and simultaneously intramuscularly or subcutaneously immunizing each duckling with the an avian influenza inactivated oil-emulsion vaccine.

Preferably, in step 1), the first immunization is performed on the ducklings at the age of 8 to 10 days.

Preferably, in step 1), the dosage of the inactivated antigens is 0.1 mL to 1 mL, and an anti-avian influenza virus antibody titer after inoculation is 7 Log2 to 12 Log2 according to hemagglutination assay (HA).

Preferably, in step 1), the dosage of the inactivated antigens is 0.3 mL to 0.5 mL, and the anti-avian influenza virus antibody titer after inoculation is 9 Log2 to 10 Log2 according to the HA.

Preferably, in step 1), the dosage of the inactivated oil-emulsion vaccines is 0.1 mL to 1 mL, and an anti-avian influenza virus antibody titer after immunization is 7 Log2 to 12 Log2 according to hemagglutination inhibition assay (HI).

Preferably, in step 1), the dosage of the inactivated oil-emulsion vaccines is 0.3 mL to 0.5 mL, and the anti-avian influenza virus antibody titer after immunization is 9 Log2 to 10 Log2 according to the HI.

Preferably, the method further includes a step 2): immunizing the ducklings after 10 days from the first immunization by inoculating each duckling with the avian influenza inactivated antigen into the abdominal cavity.

Preferably, in step 2), the dosage of the inactivated antigens is 0.1 to 1 mL, and the anti-avian influenza virus antibody titer after inoculation is 7 Log2 to 12 Log2 according to HA.

Preferably, in step 2), the dosage of the inactivated antigens is 0.3 mL to 0.5 mL, and the anti-avian influenza virus antibody titer after inoculation is 9 Log2 to 10 Log2 according to the HA.

Preferably, strains of the inactivated antigens include an H5 subtype avian influenza strain and an H9 subtype avian influenza strain; and a production strain of the inactivated oil-emulsion vaccine includes an H5 subtype avian influenza strain and an H9 subtype avian influenza strain.

Compared with the prior art, the present invention has the following beneficial effects:

1) through double effects of intraperitoneal inoculation with the avian influenza inactivated antigens and intramuscular or subcutaneous injection and immunization with the avian influenza inactivated oil-emulsion vaccines, the present invention enables ducklings to quickly produce the immune response, thereby quickly producing anti-avian influenza antibodies; and 2) the method for enabling ducklings to quickly produce the anti-avian influenza antibodies and maintain the antibody titer provided in the present invention is obviously higher in speed of producing the avian influenza antibodies than the traditional duck immunized with the avian influenza inactivated oil-emulsion vaccine, and the immune dead time of the duck immunized with the avian influenza inactivated vaccine is effectively reduced by more than 7 days.

The present invention is further described below in detail in combination with specific embodiments.

DETAILED DESCRIPTION

The present invention provides a method for enabling ducklings to quickly produce anti-avian influenza antibodies and maintain antibody titer, including: step 1) immunizing ducklings at the age of 5 to 15 days by inoculating each duckling with an avian influenza inactivated antigen in an abdominal cavity, and simultaneously intramuscularly or subcutaneously immunizing the ducklings with avian influenza inactivated oil-emulsion vaccines.

In the following specific embodiments, unless otherwise specified, the employed reagents or test objects are commercially available.

In the following specific embodiments, the employed ducklings are commercially-available local ducklings in Guangdong Province, inactivated antigens and inactivated oil-emulsion vaccines are from Guangdong Wens Dahuanong Biotechnology Co. Ltd., and an inactivated antigen strain includes an H5 subtype avian influenza strain and an H9 subtype avian influenza strain, such as H5 Re-6 strain and H9 SS strain; and the inactivated oil-emulsion vaccine is H5+H9 subtype avian influenza inactivated vaccine, and the production strain thereof includes an H5 subtype avian influenza strain and H9 subtype avian influenza strain, such as H5 Re-6 strain and H9 SS strain.

Embodiment 1

50 commercially-available newly hatched ducklings are obtained and divided into six experimental groups, wherein group 1 is a control group and is not immunized; group 2 receives first immunization at the age of one day; group 3 receives the first immunization at the age of 5 days; group 4 receives the first immunization at the age of 8 days; group 5 receives the first immunization at the age of 10 days; group 6 receives the first immunization at the age of 14 days; and groups 2 to 6 are re-immunized after 10 days from the first immunization.

For the ducklings in the experimental groups 1 to 6, blood is collected from veins under duck wings on 0, $5^{th}$, $7^{th}$, $14^{th}$, $21^{st}$, $28^{th}$, $35^{th}$ and $42^{nd}$ days after the first immunization, serum is isolated from the blood, and the titer values (HI titer values) of anti-avian influenza virus antibodies in the serum are uniformly determined. Results are shown in Table 1.

In the present embodiment, the first immunization specifically includes the following operation steps: each duckling is injected with 0.5 mL of avian influenza inactivated antigen in the abdominal cavity, and simultaneously is subcutaneously injected with 0.5 mL of avian influenza inactivated oil-emulsion vaccine in the neck.

In the present embodiment, the re-immunization treatment specifically includes the following operation step: each duckling is injected with 0.5 mL of avian influenza inactivated antigen in the abdominal cavity.

TABLE 1

Impact of Composite Immunization of Avian Influenza Inactivated Antigens and Inactivated Vaccines on Avian Influenza Antibodies of Ducklings

| Experimental group | Vaccine | Monitoring Time and Antibody Titer (HI Valence) 0 day | $5^{th}$ day | $7^{th}$ day | $14^{th}$ day | $21^{st}$ day | $28^{th}$ day | $35^{th}$ day | $42^{nd}$ day |
|---|---|---|---|---|---|---|---|---|---|
| Group 1 | H5 | 6 | 5 | 4 | 2 | 0 | 0 | 0 | 0 |
| | H9 | 4 | 3 | 2 | 1 | 0 | 0 | 0 | 0 |
| Group 2 | H5 | 6 | 5 | 4 | 2 | 3 | 4 | 4 | 3 |
| | H9 | 4 | 3 | 4 | 3 | 4 | 4 | 4 | 3 |
| Group 3 | H5 | 2 | 5 | 5 | 6 | 6 | 7 | 5 | 4 |
| | H9 | 1 | 4 | 6 | 6 | 7 | 7 | 7 | 7 |
| Group 4 | H5 | 3 | 4 | 5 | 7 | 8 | 7 | 6 | 5 |
| | H9 | 2 | 6 | 7 | 8 | 9 | 9 | 8 | 8 |
| Group 5 | H5 | 2 | 5 | 6 | 7 | 8 | 8 | 8 | 7 |
| | H9 | 1 | 6 | 7 | 8 | 9 | 9 | 8 | 8 |
| Group 6 | H5 | 2 | 5 | 6 | 7 | 8 | 8 | 8 | 7 |
| | H9 | 1 | 6 | 8 | 8 | 9 | 9 | 9 | 8 |

The results show that after the ducklings are injected with the immune avian influenza inactivated antigens in the abdominal cavities and subcutaneously injected with the inactivated oil-emulsion vaccines, after 5 days, the H5 subtype avian influenza antibody titer can reach 4 to 5 Log2, and the H9 subtype avian influenza antibody titer can reach 3 to 6 Log2; for the ducklings receiving the first immunization at the age of more than 5 days, after 7 days, the H5 subtype avian influenza antibody titer can reach 5 to 7 Log2, the H9 subtype avian influenza antibody titer can reach 6 to 8 Log2, and the titer can be maintained for more than 35 days; and for the ducklings receiving the first immunization at the age of 8 to 10 days, the avian influenza H5 and H9 subtypes avian influenza antibody titers are greater than 4 Log2 after 5 days; after 7 days, the H5 subtype avian influenza antibody titer can reach 5 to 7 Log2, the H9 subtype avian influenza antibody titer can reach 7 to 9 Log2, and the titer can be maintained for more than 42 days.

Embodiment 2

50 commercially-available newly-hatched ducklings are obtained and divided into 5 experimental groups, wherein group 1 is a control group and is not immunized.

Groups 2 to 5 receive the first immunization at the age of 15 days, wherein each duckling in group 2 receives the first immunization by means of intramuscular injection with 0.5 mL of avian influenza inactivated antigen; each duckling in group 3 receives the first immunization by means of subcutaneous injection with 0.5 mL of avian influenza inactivated antigen in the neck; each duckling in group 4 receives the first immunization by means of intranasal immunization with 0.5 mL of avian influenza inactivated antigen and each duckling in group 5 receives the first immunization by means of intraperitoneal injection with 0.5 mL of avian influenza inactivated antigen.

Groups 2 to 5 receive re-immunization after 10 days from the first immunization, and the re-immunization includes the following specific operation steps:

Blood is collected from veins under wings of the ducklings on 0, $5^{th}$, $7^{th}$, $14^{th}$, $21^{st}$, $28^{th}$, $35^{th}$ and $42^{nd}$ days after the first immunization, serum is isolated, the titer values (HI titer values) of anti-avian influenza virus antibodies in the serum are uniformly determined; and results are shown in Table 2.

TABLE 1

Effects of Different Avian Influenza Inactivated Antigen Immunization Ways on Ducklings

| Experimental group | Vaccine | Monitoring Time and Antibody Titer (HI Titer) | | | | | | | |
|---|---|---|---|---|---|---|---|---|---|
| | | 0 day | $5^{th}$ day | $7^{th}$ day | $14^{th}$ day | $21^{st}$ day | $28^{th}$ day | $35^{th}$ day | $42^{nd}$ day |
| Group 1 | H5 | 1 | 1 | 0 | 0 | 0 | 0 | 0 | 0 |
| | H9 | 2 | 1 | 0 | 0 | 0 | 0 | 0 | 0 |
| Group 2 | H5 | 1 | 2 | 3 | 1 | 0 | 0 | 0 | 0 |
| | H9 | 1.5 | 2 | 2 | 0 | 0 | 0 | 0 | 0 |
| Group 3 | H5 | 1 | 2 | 2 | 0 | 0 | 0 | 0 | 0 |
| | H9 | 2 | 3 | 3 | 2 | 1 | 0 | 0 | 0 |
| Group 4 | H5 | 1 | 3 | 2 | 1 | 0 | 0 | 0 | 0 |
| | H9 | 1 | 4 | 2 | 4 | 3 | 0 | 0 | 0 |
| Group 5 | H5 | 2 | 5 | 6.5 | 7 | 8 | 7 | 4 | 1 |
| | H9 | 1 | 6 | 7 | 8 | 9 | 8 | 5 | 2 |

It can be known from Table 2 that for the ducklings in group 5 receiving the immunization with the intraperitoneal injection way, after 5 days from the first immunization, the H5 subtype avian influenza antibody titer can reach as high as 5 Log2, and the H9 antibody titer can reach as high as 6 Log2

TABLE 3

Effects for Immunizing Ducklings with Avian Influenza Inactivated Vaccine

| Experimental group | Vaccine | 0 day | 5th day | 7th day | 14th day | 21st day | 28th day | 35th day | 42nd day |
|---|---|---|---|---|---|---|---|---|---|
| Group 1 | H5 | 2 | 2 | 1 | 1 | 0 | 0 | 0 | 0 |
|  | H9 | 1 | 1 | 1 | 0 | 0 | 0 | 0 | 0 |
| Group 2 | H5 | 1 | 1 | 2 | 2 | 3 | 4 | 5 | 5 |
|  | H9 | 1.5 | 2 | 3 | 4 | 5 | 6 | 6 | 6 |
| Group 3 | H5 | 1 | 2 | 3 | 4 | 5 | 6 | 6 | 6 |
|  | H9 | 1.5 | 2 | 4 | 7 | 8.5 | 8 | 8.5 | 8 |
| Group 4 | H5 | 2 | 1 | 2 | 3 | 5 | 6 | 7 | 6 |
|  | H9 | 1 | 1 | 3 | 6 | 8 | 8.5 | 9 | 9 |
| Group 5 | H5 | 0.5 | 1 | 2 | 3 | 5 | 6 | 6 | 6 |
|  | H9 | 0.5 | 2 | 5 | 6 | 8 | 9 | 9 | 8 |

It can be known from Table 4 that after 21 days from that the ducklings are immunized with the avian influenza inactivated vaccine, the H5 subtype avian influenza specific antibody valence (H1 valence) is 3 to 5 Log2 and the H9 subtype avian influenza specific antibody valence (H1 valence) is 5 to 8 Log2; and the avian influenza specific antibody valences are relatively low after 0 to 14 days from the immunization and insufficient to play a role in immune protection.

The above embodiments are only preferred embodiments of the present invention and may not be used to limit the protection scope of the present invention. Any insubstantial variations and replacements made by those skilled in the art based on the present invention shall fall within the protection scope claimed by the present invention.

We claim:

1. A method for enabling ducklings to produce anti-avian influenza antibodies and maintain antibody titer, comprising: step 1) performing first immunization on ducklings at the age of 5 to 15 days by inoculating each duckling with an avian influenza inactivated antigen into an abdominal cavity, and simultaneously intramuscularly or subcutaneously immunizing each duckling with an avian influenza inactivated oil-emulsion vaccine.

2. The method according to claim 1, wherein in step 1), the first immunization is performed on the ducklings at the age of 18 to 10 days.

3. The method according to claim 1, wherein, in step 1), the dosage of the inactivated antigens is 0.1 to 1 mL, and an anti-avian influenza virus antibody titer after inoculation is 7 Log2 to 12 Log2 according to hemagglutination assay.

4. The method according to claim 1, wherein, in step 1), the dosage of the inactivated antigens is 0.3 mL to 0.5 mL, and the anti-avian influenza virus antibody titer after inoculation is 9 Log2 to 10 Log2 according to the hemagglutination assay.

5. The method according to claim 1, wherein, in step 1), the dosage of the inactivated oil-emulsion vaccines is 0.1 mL to 1 mL, and an anti-avian influenza virus antibody titer after immunization is 7 Log2 to 12 Log2 according to hemagglutination inhibition assay.

6. The method according to claim 1, wherein, in step 1), the dosage of the inactivated oil-emulsion vaccines is 0.3 mL to 0.5 mL, and the anti-avian influenza virus antibody titer after immunization is 9 Log2 to 10 Log 2 according to the hemagglutination inhibition assay.

7. The method according to claim 1, further comprising: step 2) re-immunizing the ducklings after 10 days from the first immunization by inoculating each duckling with the avian influenza inactivated antigen into the abdominal cavity.

8. The method according to claim 7, wherein in step 2), the dosage of the inactivated antigens is 0.1 mL to 1 mL, and the anti-avian influenza virus antibody titer after inoculation is 7 Log2 to 12 Log2 according to hemagglutination assay.

9. The method according to claim 7, wherein, in step 2), the dosage of the inactivated antigens is 0.3 mL to 0.5 mL, and the anti-avian influenza virus antibody titer after inoculation is 9 Log2 to 10 Log2 according to the hemagglutination assay.

10. The method according to claim 1, wherein in the step 1), strains of the inactivated antigens comprise an H5 subtype avian influenza strain and an H9 subtype avian influenza strain; and a production strain of the inactivated oil-emulsion vaccine comprises an H5 subtype avian influenza strain and an H9 subtype avian influenza strain.

* * * * *